United States Patent [19]
Mazess et al.

[11] Patent Number: 6,081,582
[45] Date of Patent: Jun. 27, 2000

[54] TRANSVERSE SCANNING DENSITOMETER

[75] Inventors: Richard B. Mazess; Joseph P. Bisek, both of Madison; David L. Ergun, Verona; Robert A. Washenko, Madison, all of Wis.

[73] Assignee: Lunar Corporation, Madison, Wis.

[21] Appl. No.: 09/187,535

[22] Filed: Nov. 6, 1998

Related U.S. Application Data

[63] Continuation-in-part of application No. 08/703,250, Aug. 26, 1996, Pat. No. Re. 36,162, which is a continuation-in-part of application No. 07/976,797, Nov. 16, 1992, Pat. No. 5,287,546, which is a continuation-in-part of application No. 07/944,626, Sep. 14, 1992, Pat. No. 5,228,068.

[51] Int. Cl.[7] ................................................. G01B 15/02
[52] U.S. Cl. .......................... 378/146; 378/98.12; 378/54
[58] Field of Search ............................... 378/62, 145, 146, 378/193, 195, 196, 197, 198, 54, 55, 56, 98.12

[56] References Cited

U.S. PATENT DOCUMENTS

| Re. 36,162 | 3/1999 | Bisek et al. | 378/146 |
|---|---|---|---|
| 5,305,368 | 4/1994 | Bisek et al. | 378/146 |
| 5,432,834 | 7/1995 | Gershman | 378/196 |
| 5,715,820 | 2/1998 | Stein et al. | 600/407 |
| 5,797,396 | 8/1998 | Geiser et al. | 128/653.1 |
| 5,838,765 | 11/1998 | Gershman et al. | 378/196 |

FOREIGN PATENT DOCUMENTS

WO 97/40737  6/1997  WIPO.

OTHER PUBLICATIONS

Blake, G.M., Parker, J.C., Buxton, F.M.A. and Fogelman, I., "Dual X–ray absorptiometry: a comparison between fan beam and pencil beam scans," (1993) *The British Journal of Radiology*, 66:902–906.

Eiken, P., Bärenholdt, Jensen, L.B., Gram, J. and Nielsen, S.P., "Switching from DXA Pencil–Beam to Fan–Beam. I: Studies In Vitro at Four Centers," *Bone*, 15:667–670 (1994).

Eiken, P., Kolthoff, N., Bärenholdt, O., Hermansen, F., and Nielsen, S.P., "Switching from DXA Pencil–Beam to Fan–Beam. II: Studies In Vivo," *Bone*, 15:671–676 (1994).

Griffiths, M.R., Noakes, K.A. and Pocock, N.A., "Correcting the Magnification Error of Fan Beam Densitometers," *Journal of Bone and Mineral Research*, 12:119–123 (1997).

Pocock, N.A., Noakes, K.A., Majerovic, Y. and Griffiths, M.R., "Magnification Error of Femoral Geometry Using Fan Beam Densitomers," *Calcif. Tissue Int.*, (1997) 60–8–10.

*Primary Examiner*—David P. Porta
*Attorney, Agent, or Firm*—Quarles & Brady

[57] ABSTRACT

A scanning densitometer provides transverse scanning of the patient with a small angle fan beam to significantly reduce parallax and image overlap blurring. Additional reduction of artifacts in the region of combined scans is obtained by a varying overlap of the scans when they are merged determined by a best matching of an identified structure within the scan. The matching process which reveals an ideal overlap provides height data of the structure allowing correction of magnification for structures which change in height within the patient over the scan.

39 Claims, 4 Drawing Sheets

TRANSVERSE SCANNING DENSITOMETER

CROSS-REFERENCE TO RELATED APPLICATIONS

This application is a continuation-in-part of U.S. application RE Ser. No. 08/703,250 filed Aug. 26, 1996 and entitled METHOD AND APPARATUS FOR PIECE-WISE RADIOGRAPHIC SCANNING now RE Ser. No. 36,162 which is reissue of U.S. Pat. No. 5,305,368 issued Apr. 19, 1994 which is a continuation-in-part of U.S. application Ser. No. 976,797 filed Nov. 16, 1992 now issued as U.S. Pat. No. 5,287,546 which is a continuation-in-part of U.S. application Ser. No. 944,626 filed Sep. 14, 1992 now issued as U.S. Pat. No. 5,228,068.

STATEMENT REGARDING FEDERALLY SPONSORED RESEARCH OR DEVELOPMENT

BACKGROUND OF THE INVENTION

The field of the invention relates generally to radiographic instruments and more particularly to a scanning bone densitometer in which measurements of a patient are acquired in a series of overlapping scans.

Scanning radiographic equipment differs from conventional radiography in that it employs a narrowly collimated beam of radiation, typically x-rays, formed into, for example, a fan beam, rather than a broad area cone beam. The compact beam size allows the replacement of an image forming sheet of radiographic film, used with conventional radiographic equipment, with a small area array of electronic detector elements. Further the scanning allows the collection of data over a much broader area than would be practical with a single x-ray cone beam.

The electronic detector elements receiving the transmitted radiation produce electrical signals which may be converted to digital values by an analog to digital converter for the later development of an image or for other processing by computer equipment. The ability to quantify the measurement of the transmitted radiation, implicit in the digitization by the analog to digital converter, allows not only the formation of a radiographic "attenuation" image but also the mathematical analysis of the composition of the attenuating material by dual energy techniques. See generally, "Generalized Image Combinations in Dual KVP Digital Radiography" by Lehmann et al., Med. Phys. 8(5) Sept/Oct. 1981. Such dual energy techniques quantitatively compare the attenuation of radiation at two energies to distinguish, for example, between bone and soft tissue. This makes possible the measurement of bone mass, such measurement being important in the treatment of osteoporosis and other bone diseases.

The compact beam of radiation used in scanning radiographic systems allows the use of limited area detectors permitting high resolution with relatively lower cost. Further, the images formed by a compact beam are potentially more accurate than those produced by a typical broad beam radiographic system. The accuracy arises from the limited divergence of the rays of the beam as compared to a broad area cone beam. This narrow collimation of the fan beam reduces "parallax" in the projected image, particularly of anatomical planar surfaces that are nearly parallel with the central ray of the beam—such as the superior and inferior borders of the vertebra in the spine.

The compact beam of radiation, however, also requires increased scanning motion if large areas are to be measured. In a fan beam system, typically the fan beam will be scanned in a raster or "zig-zag" pattern over the area to be measured, each line of the scan forming a scan image separated by somewhat less than the width of the fan beam to ensure complete illumination of the entire volume of the imaged object. The direction of scanning is generally perpendicular to the direction of the radiation and the plane of the fan beam.

U.S. Pat. No. 5,305,368 entitled Method and Apparatus for Piece-Wise Radiographic Scanning issuing Apr. 19, 1994 assigned to the assignee of the present invention and hereby incorporated by reference, describes the creation of a single image, or quantitative data set, from a plurality of scan images acquired across a patient, either longitudinally aligned with the superior-inferior axis of the patient or transversely from the patient's left to right.

Transverse scanning provides the advantage that the time between the acquisition of adjacent scan images is minimized (because the transverse direction across the patient is shorter than the longitudinal direction across the patient). This reduces the severity of patient motion artifacts between scan images allowing them to be more accurately merged. A drawback to transverse scanning, however, is that the diverging beams of radiation used in the scanning creates triangular regions of overlap between adjacent scans.

As disclosed in the '368 patent, this overlap between adjacent scans distorts or blurs the imaged produced by combining the scan images near the edges of the scan images. The blurring is caused by a dependency of the projected image on the height of the imaged structure (the "height dependency problem") that displaces the relative position of the structure in the two scan image as a result of the different angles of illumination of the structure by the adjacent beams of radiation.

The '368 patent discloses weighting the edge portions of adjacent scan images to prevent a disproportionate contribution by redundant data of these overlapping edge portions to the combined image. The weighting assigns to the corresponding portions of two overlapping regions, weighting factors that sum to one. Each pixel of the overlapping region, may for example, be multiplied by a weighting factor of 0.5.

It has been suggested by some that a weighting system like that of the '368 patent, may solve the height dependency problem. However, as noted in the '368 patent, a weighting and combining alone necessarily blurs the image and is less preferred for diagnosis and measurement than some misregistration in the combined image.

Accordingly, the '368 patent teaches the use of a longitudinal scanning in which the fan beams of adjacent scans are angled to eliminate the height dependency problem. Such a correction may be performed for longitudinal scans of the patient where a single wide angle fan beam may be used but is impractical for a transverse scanning of the patient where the creation of a single fan beam would entail too great an angular dispersion between individual rays of the beam.

Ideally, a scanning densitometry system might employ a combination of transverse scanning for the reduction of patient motion artifacts while reducing height dependency problems.

BRIEF SUMMARY OF THE INVENTION

The present invention provides a system suitable for transverse scanning of an entire patient that substantially eliminates the height dependency problem using a combination of an extremely compact fan beam and a mathematical merging of the scan images employing a height sensitive overlapping of the images and a height sensitive magnification of the images wholly separate from image weighting known in the prior art.

The small angle fan beam as an initial matter significantly reduces parallax and height dependency problems when the images are merged together. Further the images for each scan are merged together with different amounts of overlap determined from an analysis of the image itself, for example, using a correlation between adjacent bone structures in different scan images. This correlation reveals the height of the image structure allowing for correction of magnification. Correction of magnification provides for more accurate quantitative measurement of quantities that are magnification dependent such as bone density.

Specifically then, the present invention provides for a scanning bone densitometer having a radiation source collimated to produce a beam of radiation directed across a patient to an electronic detector, the latter which measures the beam of radiation passing through the patient. A scanning assembly moves the radiation source and electronic detector along a series of scan paths across the patient to acquire a plurality of scan images. An electronic computer then receives the scan images and executes a stored program to determine a degree of image alignment of at least a portion of adjacent scan images for different overlaps and merges the adjacent scan images with an overlap corresponding to a best matching of the scan images.

Thus it is one object of the invention to provide improved merging of scanned images in a scanning densitometer by allowing different degrees of overlap to better match structures within the images having various heights within the patient.

The degree of image alignment may evaluate only the bone portion of the image.

Thus it is another object of the invention to improve the ability to match the images by eliminating structure such as soft tissue whose matching is not critical.

The electronic computer may further deduce a structure height based on a known divergence of the radiation beams and the determined overlap providing the best degree of image alignment. The height may be used to scale each scan image prior to merging adjacent scan images.

Thus it is another object of the invention to employ the difference in overlap between adjacent scan images to correct the magnification of the image.

The patient support may support a supine patient with the patient's head and feet lying along a longitudinal axis and the scanning assembly may move the radiation source and electronic detector along a series of transverse scan paths substantially perpendicular to the longitudinal axis across the patient to acquire the scan images.

Thus it is another object of the invention to permit a transverse scanning of the patient such as may reduce motion artifacts between adjacent scan images.

Prior to merging, the images may be weighted so as to eliminate any disproportionate influence of redundant data in the images.

Thus it is another object of the invention to provide a system which does not rely on weighting alone such as may produce a blurring of the merged image if not used with correcting of overlap of the images per the present invention.

The foregoing and other objects and advantages of the invention will appear from the following description. In the description, reference is made to the accompanying drawings which form a part hereof and in which there is shown by way of illustration a preferred embodiment of the invention. Such embodiment does not necessary represent the full scope of the invention, however, and reference must be made to the claims herein for interpreting the scope of the invention. Variations of the invention within the scope of the claims may achieve less than all of the above objects.

DETAILED DESCRIPTION OF THE INVENTION

Figure 1:
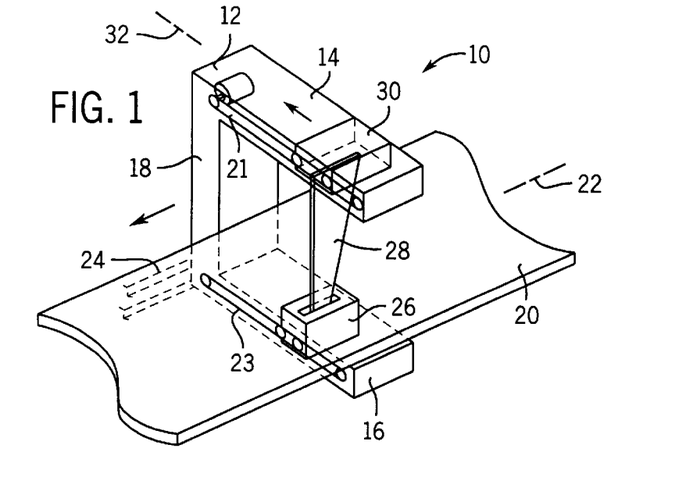
FIG. 1 is a perspective view of a transverse scanning densitometer of the present invention showing a support arm holding a radiation source and detector in vertical opposition about a patient support table.

Referring now to FIG. 1, a densitometer 10 of the present invention includes a support arm 12 having vertically opposed horizontal arms 14 and 16 separated by vertical bar 18. Between the arms 14 and 16 is a horizontal planar patient support table 20 extending along a longitudinal axis 22. A belt drive system 24 of a type well known in the art allows motion of the arm 12 longitudinally along axis 22 for the length of the table 20.

Positioned within the lower arm 16 is an x-ray source 26 providing a collimated fan beam 28 of x-rays directed upward through the table 20 to the arm 14 where it may be received by a linear detector 30. The fan beam 28 is oriented so that its narrowest extent is along the transverse axis and its widest extent along the longitudinal axis 22. The table 20 is generally radiolucent so as to provide a support surface without significantly affecting the attenuation of the fan beam 28.

The x-ray source 26 and linear detector 30 may be moved transversely along transverse axis 32 as encased in arms 16 and 14, respectively, so as to provide transverse scans of the patient on the table 20. Motion of the x-ray source 26 and detector 30 is synchronized by belt drive actuation mechanisms 21 held within arms 16 and 14 as will be well understood to those of ordinary skill in the art.

Figure 2:
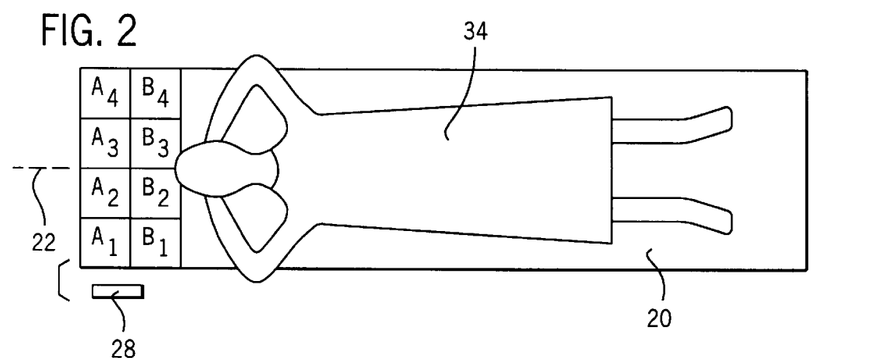
FIG. 2 is a top plan view of the table of FIG. 1 showing a positioning of the patient for transverse scanning and showing the direction of the transverse scanning.

Referring now to FIG. 2, fan beam 28 may be scanned over the surface of table 20 and hence may scan the whole body of patient 34 so as to generate a series of transversely extending scan images that may be merged into a single image or data set. For example, a first scan image may encompass in sequence areas A1, A2, A3, and A4. At the end of this scan, motion of the arm 12 in the longitudinal direction may be had so that the detector 30 may scan a second scan image comprising in order areas B4, B3, B2 and B1. Because the transverse width of the patient is substantially less than the superior to inferior height of the patient, each scan image, e.g., areas A or areas B is acquired at a time closely proximate to its adjacent scan images and thus the risk of patient motion and the amount of patient motion may be substantially reduced.

The radiation source 26 may be a radioisotope but is preferably an x-ray tube running at constant voltage to produce a poly-energetic radiation beam. The beam may be subsequently filtered with a K-edge filter to form two energy modes. Alternatively, the radiation source 26 may be an x-ray tube run in a switched voltage mode where the voltage on the x-ray tube is periodically changed from a high to low voltage shifting the energy spectrum of the produced x-ray beam. Data is acquired by a broad band detector and is sequentially high and low energy data as may be used in dual energy measurements. Other techniques including rotating filter wheels and the like may be used to produce sequential dual energy beams.

Figure 3:
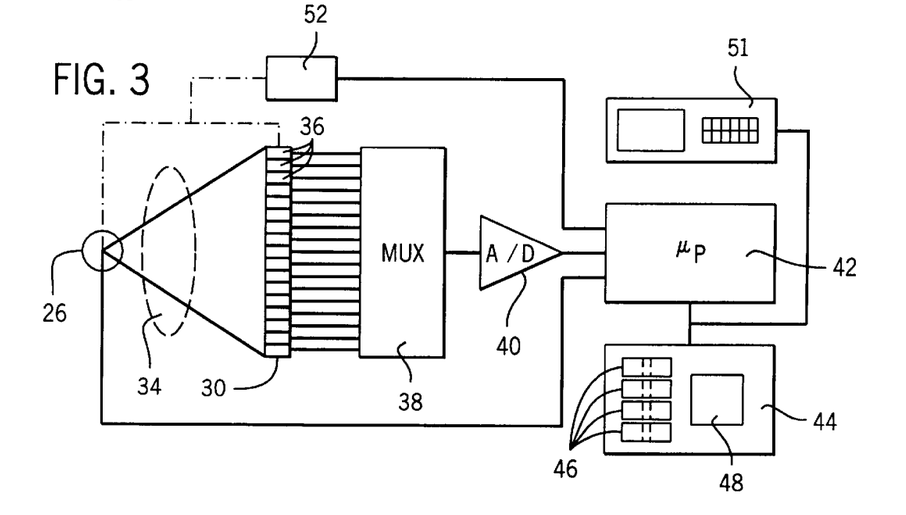
FIG. 3 is a block diagram of the densitometer of FIG. 1 showing a computer communicating with the radiation source and detector of FIG. 1, and for communicating with a scanning mechanism for control of the transverse scanning of FIG. 2.

Referring now to FIG. 3, when the x-ray source 26 is poly-energetic, the detector 30 may be comprised of a linear array of detector elements 36 each constructed of a crystal of cadmium zinc telluride (CZT). The crystals can alternatively comprise cadmium telluride, mercuric iodide, geranium, silicon or other x-ray sensitive materials. As is known in the art, CZT crystals, however, provide good energy and spatial resolution and can operate at room temperature and can be manufactured in large volumes in a variety of dimensions. The CZT crystals convert x-rays received into a electrical charge pulses, the amplitude of which are indicative of the energy of the x-ray absorbed. Hence, energy discrimination can be accomplished by pulse height discrimination according to techniques well known in the art such as have been used with scintillator/photo multiplier tube combinations. The pulse height signals are received by a multiplexer 38 and then converted by an A to D converter 40 to digital words that may be received by microprocessor 42 contained with the densitometer 10. The microprocessor 42 may perform the height discrimination.

Alternatively when the x-ray source 26 is poly-energetic, discrimination between high and low energy attenuation of x-rays by the patient can be done with side linear array detectors in which two transversely separated rows of detectors (comprised of a photodetector such as a photodiode and scintillator) are selectively sensitive to low energies and high energies. In this case, during a scan, each row forms either a low or high energy image, and these two images are aligned and mathematically combined to produce the necessary bone density information according to mathematical algorithms known in the art.

In an alternative design, the detector 30 can be a stacked array detector in which elements stacked along the direction of propagation of the radiation are selectively sensitive to low and high energy spectrums, respectively. A particular advantage of the stacked array detector is that it can easily accommodate a multi-linear array or area detector design such as may also be used in the present invention with a cone beam x-ray. Such stacked detectors are described and claimed in Barnes, U.S. Pat. Nos. 4,626,688 and 5,138,167, incorporated herein by reference. The signals from these detectors again are received by a multiplexer 38 and then converted by an A to D converter 40 to digital words that may be received by microprocessor 42.

In all cases the detectors include a plurality of independent detector elements, no less than three and normally greater than eight, arranged along at least one line to provide a scan image of substantial width.

Once the scan is complete, the dual energy signals provided by the detector 30 are deconstructed into images of two basis materials, such as bone or soft tissue, as is well understood in the art. The high and low energy signals can also be combined to provide a single energy mode having superior signal to noise ratio for imaging purposes.

The microprocessor 42 communicates with a memory 44 storing the data acquired during the scanning as a series of scan images 46 and holding a stored program 48 which may be executed by the microprocessor 42 to effect various control strategies and image processing as will be described. The microprocessor 42 and memory 44 also communicate with a control console 51 providing output to an operator and allowing for operator input. Further the microprocessor 42 communicates with a standard stepper motor or servo actuation mechanism 52 which includes the belt drives 24 and 21 for moving the arm 12 with respect to the table. The computer 42 may also control the x-ray source 26 either switching it between x-ray energies by controlling its voltage or controlling the fluence or flux of the x-rays by current control to effect exposure control.

Figure 4:
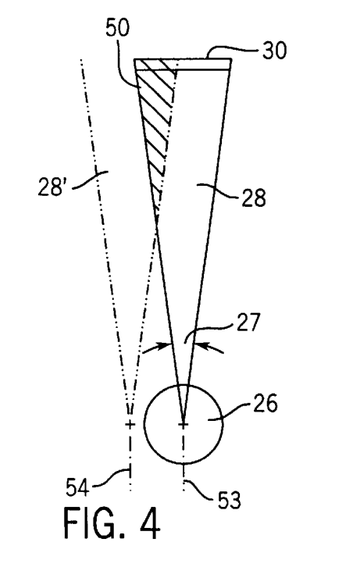
FIG. 4 is a schematic elevational representation of the x-ray source and linear detector of FIG. 1 showing the divergence angle of a fan beam of radiation and a region of overlap in the fan beam for adjacent scan images.

Referring now to FIG. 4, the fan beam 28 diverges slightly as it passes from a focal spot of the x-ray source 26 to the detector 30. In the present invention, the fan beam 28 is collimated to reduce this divergence to a value of less than 10° and preferably to approximately 4° so as to reduce parallax and height dependency problems found in an triangular overlap region 50 formed by the intersection of the volumes of the swept fan beams for successive transverse scans. The increased numbers of overlap regions 50 required by the small fan beam angle are rendered acceptable by the reduced parallax of the beams and additional imaging processing steps to be described. Generally, the overlap region 50 is formed by the intersection of the area of the fan beam 28 when the x-ray source and detector 30 are in a first position 52 to acquire a first scan image and the area of the fan beam 28' when moved to an adjacent second longitudinal position 54 to acquire a second scan image.

Figure 5:
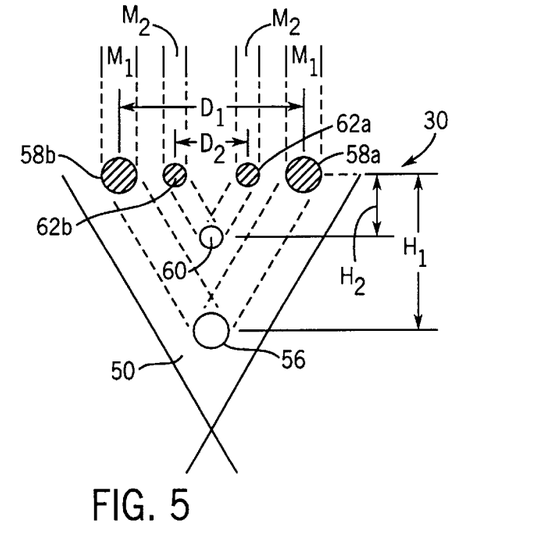
FIG. 5 is an exaggerated elevational view of the overlap region of FIG. 4 showing the displacement of images of structures within the overlap region as a function of the structure's height, and showing different magnifications of the images of structures as a function of the structures height, such as creates blurring in the region of overlap.

Referring now to FIG. 5, an object 56 positioned at a height $H_1$ from the detector 30 within the overlap region 50 will produce two projected images 58(*a*) and 58(*b*) at the detector 30 caused by the illumination of the object 56 at two different angles from the x-ray source 26 in the first longitudinal position 53 (shown in FIG. 4) and the second longitudinal position 54 (shown in FIG. 4). These projected images will have a separation $D_1$ and will have a magnification $M_1$ proportional to height $H_1$. Correspondingly, a different object 60 positioned at a lower height $H_2$ from the detector 30 will produce two images 62(*a*) and 62(*b*) having a lesser separation $D_2$ and lesser magnification $M_2$ also proportional to height $H_2$. Images 62(*b*) and 62(*a*) or 58(*a*)

and 58(b) will generally be divided into separate scan images. It will be understood that simply weighting these two scan images and then combining spatially displaced images 62(b) and 62(a) or 58(a) and 58(b) will generally cause a blurring and inaccuracy in the reproduced image and its quantitative measurements.

Accordingly, the present invention augments well known weighting techniques with a sliding of the scan images with respect to each other so as to juxtapose images 58(a) and 58(b) or 62(a) and 62(b) thereby reducing or eliminating the blurring of combining these images. The amount by which the scan images must be overlapped will depend on the initially unknown height of the imaged object 56 or 60 and therefore is determined by a matching processing as will be described.

Figure 7:
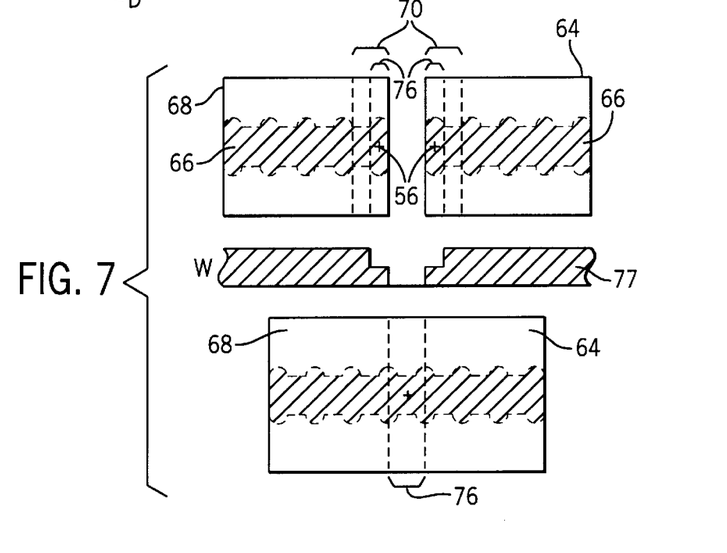
FIG. 7 is a view of two scanned images before and after merging according to an overlap distance deduced per FIG. 6 and showing a weighting of the region of overlap.

Referring now to FIG. 7, a first scan image 64 may be obtained with a transverse scan such as that at first longitudinal position 53 as shown in FIG. 4 and shows an object 56, in this case, a portion of a spinal column 66 that is also imaged in a second scan image 68 acquired along second longitudinal position 54 as shown in FIG. 4. Adjacent edges of scan images 64 and 68 have overlap portions 70 that are known functions of the size of the raster scan (the longitudinal increment) and the known divergence of the fan beam 28. Nevertheless, the exact position of objects 56 within the overlap portion 70 of images 68 and 66 will vary depending on the height of the object 56 as described with respect to FIG. 5. Accordingly, images 68 and 64 must be shifted longitudinally with respect to each other to overlap by an arbitrary amount to bring objects 56 into alignment.

Figure 6:
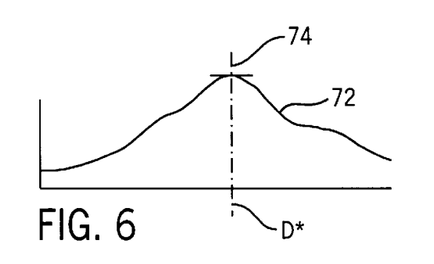
FIG. 6 is a plot of correlation versus a distance D of overlap between scan images for a typical pair of scan images.

Referring now to FIG. 6, the necessary amount of overlap may be determined by moving the images 68 and 64 into incrementally increased overlap and at each increment of overlap calculating the correlation between overlapping pixels of the images 68 and 64. This correlation process will produce a curve 72 showing a maximum correlation 74 at a given value of overlap D*.

It will be recognized that optionally the correlation may be performed not only with varying degrees of longitudinal overlap between the scanned images but with varying degrees of transverse displacement between the scanned images thereby correcting for small degrees of patient motion as well as structure height. This transverse correlation is mathematically orthogonal to the longitudinal correlation and thus does not affect the height calculation to be described below.

This value of D* will define a desired overlap 76 less than the overlap portions 70 as dictated by the height of the object 56. The desired overlap 76 is used to define a weighting mask 77 having a value of 1 in all regions of the images 68 and 64 except for the desired overlap 76 where the weighting mask has a value less than 1. The values of the weighting mask must sum to 1 for corresponding regions of desired overlap 76 for the different scan images 64 and 68. For example, each region of desired overlap 76 may be weighted by 50% or other blending curves well known in the art may be used.

The images 68 and 64 may then be merged or combined according to the overlap amount D* and the weighting mask 77, so as to produce a unitary data set which may be analyzed or displayed.

The amount of overlap D* next may be used to deduce the height of the object 56 by simple trigonometric means. The height may be used to scale the image so as to provide constant magnification to the imaged object 56 on a piecewise basis for each transverse scan. This constant magnification is important in the quantitative use of the image so as to provide a normalized basis for density measurements and improves the clarity of the image by causing the magnification of merged regions to be similar.

Figure 8:
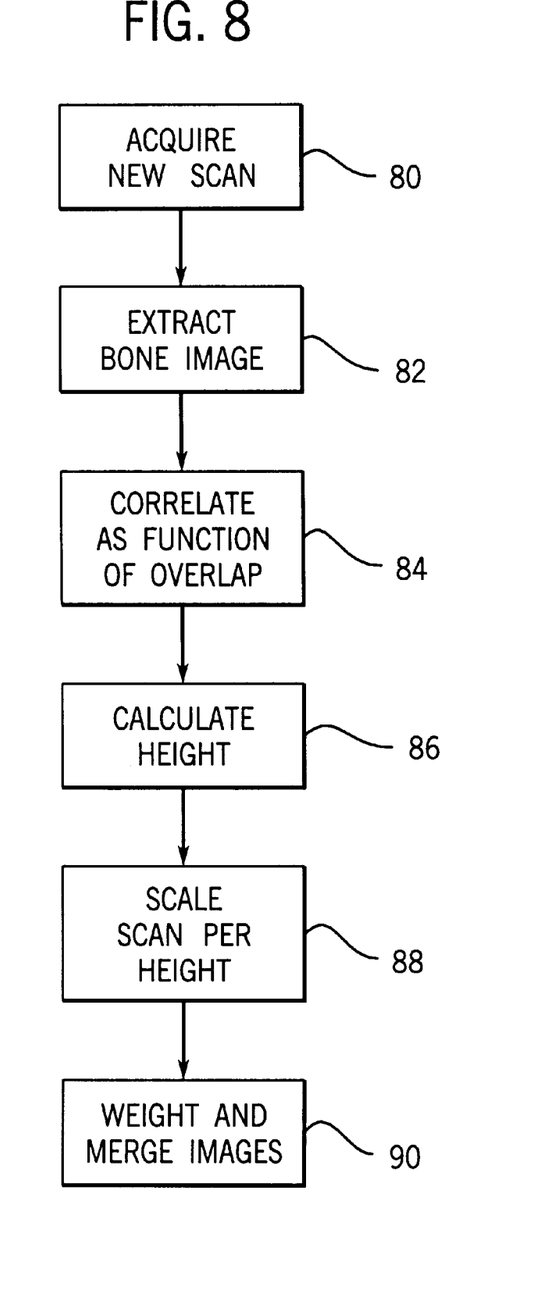
FIG. 8 is a flow chart of the steps performed by the computer of FIG. 3 in merging adjacent scan images per the present invention.

Referring now to FIG. 8, the present invention acquires successive transverse scans as indicated by process block 80 to produce scan images 64 and 68 having overlap portions 70 and shown in FIG. 7. At a succeeding process block, a bone image is extracted from each of the scan images 64 and 68 so as to highlight the image object 56 of relevance in the measurement. According to succeeding process block 84, the data of the adjacent scan images 64 and 66 within the overlap portions 70 are then correlated for a series of overlaps of progressively greater longitudinal amount to deduce an optimal or best fit overlap D* for the particular imaged object 56. It will be recognized that to the extent that imaged object 56 has varying or multiple height within the overlap portions 70, this best fit will in fact reflect an average of that height.

The height itself is calculated at process block 86 using simple trigonometric identities relying on the known average angle of the radiation within the overlap region 50 as shown in FIG. 5 and the separation of the images 58(a) and 58(b) as reflected by the value D*. This height is used at succeeding process block 88 to scale the image 64 or 68 so as to provide a predetermined constant magnification to the object 56. This correction for scaling provides increased accuracy to quantitative uses of the data, for example, in density measurements and provides improved merging of the image data to the extent that both images have similar magnification. Finally at process block 90, images are weighted with the weighting mask 77 shown in FIG. 7 and merged to create to a single file of image data.

This process is repeated as successive scans are obtained or at the conclusion of the entire scanning process off-line.

Figure 9:
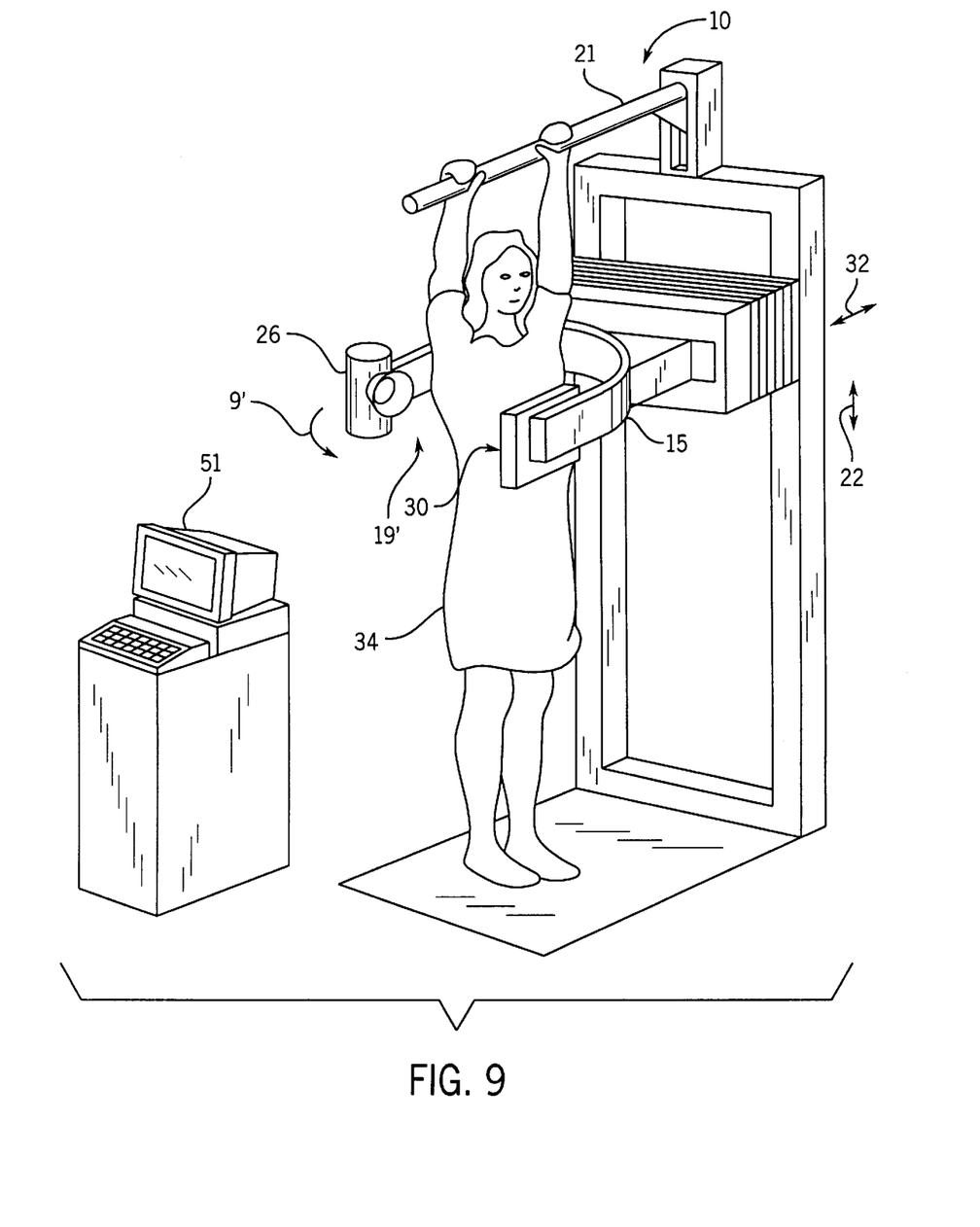
FIG. 9 is a schematic illustration of an alternative embodiment of the densitometer of FIG. 1 in which the patient is scanned in a standing position.

Referring now to FIG. 9, in a second embodiment of the densitometer 10 preferable for use in studies where the patient's spine and other bones should be under the natural load imposed by the weight of the patient's body, the patient 34 remains in a standing position with the hands above the head resting on a horizontal grip bar 21 positioned above the patient's head. The grip bar 21 serves to position and stabilize the patient between the x-ray source 26 and detector 30. In this embodiment, the x-ray source 26 and detector 30 may also rotate about a vertical axis on a C-arm 15 on which they are mounted in a horizontal plane as indicated by arrow 9'.

The C-arm 15 may be moved vertically along the patient's body along longitudinal axis 22 and may be translated in a horizontal plane to provide transverse scanning along transverse axis 32 to provide complete flexibility in producing overlapping scan images of the patient 34 for studies that involve a wider path than is subtended by the detector 13. In other respects, the vertically oriented digital x-ray device 10' operates analogously to its horizontal counterpart shown in FIG. 1.

A single densitometer 10 may be advantageously employed for both standing and supine studies of the patient 16 by incorporating a pivot (not shown) in the supporting structure of the densitometer 10 so that it may swing from the vertical position of FIG. 9 to the horizontal position of FIG. 1 for the different types of studies. It will be understood to those of ordinary skill in the art that the other components of the devices of FIG. 1 and FIG. 9 are common to both machines and thus that this pivoting design may provide a flexible, cost effective single machine.

The above description has been that of a preferred embodiment of the present invention, it will occur to those that practice the art that many modifications may be made without departing from the spirit and scope of the invention. It will be recognized that the above technique of acquiring and merging images may be used for longitudinal scanning as well as transverse scanning and that further the individual corrections of overlap adjustment and magnification correction are in fact independent and can be used in a system individually without the other. It is contemplated that many different types of solid state energy detectors will be developed in the next few years and the invention should not be considered limited to the detectors described except as provided in the claims. In order to apprise the public of the various embodiments that may fall within the scope of the invention, the following claims are made.

We claim:

1. A scanning bone densitometer comprising:
   a radiation source collimated to produce a beam of radiation;
   a radiation detector positioned with respect to the radiation source to receive the beam of radiation passing through a patient;
   a scanning assembly moving the radiation source and radiation detector along a series of scan paths across the patient to acquire a plurality of scan images; and
   an electronic computer communicating with the radiation detector and executing a stored program to:
      (i) determine a degree of image alignment, of at least a portion of adjacent given scan images by sliding the scan images to different overlaps of the adjacent scanned images;
      (ii) merge the adjacent given scan images with an overlap corresponding to a best degree of image alignment.

2. The densitometer of claim 1 including a patient support table sized and positioned to support the patient in a supine position positioned between the radiation source and radiation detector.

3. The densitometer of claim 1 wherein the radiation source and radiation detector are positioned to provide a space wherein the patient may stand during a scanning of the patient by the scanning assembly.

4. The densitometer of claim 1 wherein the electronic computer executes the stored program to remove from the adjacent scanned images non-bone structures prior to determining a degree of image alignment.

5. The densitometer of claim 1 wherein the patient support supports a supine patient with the patient's head and feet lying along a longitudinal axis and wherein the scanning assembly moves the radiation source and radiation detector along a series of transverse scan paths substantially perpendicular to the longitudinal axis across the patient to acquire the scan images.

6. The densitometer of claim 1 further wherein the radiation source is collimated to produce a fan beam of radiation and wherein the radiation detector is a linear array of detector elements.

7. The densitometer of claim 6 wherein the linear array of detector elements are CZT detector elements.

8. The densitometer of claim 6 wherein the linear array of detector elements are stacked layers of scintillators having different energy sensitivities each associated with a photodetector.

9. The densitometer of claim 6 wherein the linear array of detector elements are side by side rows of scintillators having different energy sensitivities each associated with a photodetector.

10. The densitometer of claim 1 wherein the radiation source is an x-ray tube having a switched voltage to produce sequentially different x-ray energies.

11. The densitometer of claim 1 wherein the degree of image alignment is determined by a correlation between the portions of adjacent scan images.

12. The densitometer of claim 1 wherein the electronic computer executes the stored program to apply a reduced weight to portions of the adjacent scan images overlapping in the merged images.

13. The densitometer of claim 1 wherein the electronic computer further executes the stored program to scaling the at least one of the given scan images according to the structure height prior to merging the adjacent scan images.

14. A scanning bone densitometer comprising:
    a radiation source collimated to produce a diverging beam of radiation;
    a radiation detector positioned with respect to the radiation source to receive the beam of radiation passing through a patient;
    a scanning assembly moving the radiation source and radiation detector along a series of scan paths across the patient held by the patient support to acquire a plurality of scan images; and
    an electronic computer communicating with the radiation detector and executing a stored program to:
       (i) determine a degree of image alignment for at least a portion of adjacent given scan images by sliding the scan images to different overlaps of the adjacent scanned images;
       (ii) for at least one of the given scan images deducing a structure height based on the beam divergence and the overlap providing best degree of image alignment;
       (iii) scaling the at least one of the given scan images according to the structure height; and
       (iv) merging the scaled scan image with the other of the adjacent scan images.

15. The densitometer of claim 14 including a patient support table sized and positioned to support the patient in a supine position positioned between the radiation source and radiation detector.

16. The densitometer of claim 14 wherein the radiation source and radiation detector are positioned to provide a space wherein the patient may stand during a scanning of the patient by the scanning assembly.

17. The densitometer of claim 14 wherein the electronic computer executes the stored program to remove from the adjacent scanned images non-bone structures prior to determining a degree of image alignment.

18. The densitometer of claim 14 wherein the patient support supports a supine patient with the patient's head and feet lying along a longitudinal axis and wherein the scanning assembly moves the radiation source and radiation detector along a series of transverse scan paths substantially perpendicular to the longitudinal axis across the patient to acquire the scan images.

19. The densitometer of claim 14 further wherein the radiation source is collimated to produce a fan beam of radiation and wherein the radiation detector is a linear array of detector elements.

20. The densitometer of claim 19 wherein the linear array of detector elements are CZT detector elements.

21. The densitometer of claim 19 wherein the linear array of detector elements are stacked layers of scintillators having different energy sensitivities each associated with a photodetector.

22. The densitometer of claim 19 wherein the linear array of detector elements are side by side rows of scintillators having different energy sensitivities each associated with a photodetector.

23. The densitometer of claim 14 wherein the radiation source is an x-ray tube having a switched voltage to produce sequentially different x-ray energies.

24. The densitometer of claim 14 wherein the degree of image alignment is determined by a correlation between the portions of adjacent scan images.

25. The densitometer of claim 14 wherein the electronic computer executes the stored program to apply a reduced weight to portions of the adjacent scan images overlapping in the merged images.

26. The scanning densitometer of claim 1 wherein the radiation source is poly-energetic radiation beam filtered with a K-edge filter to form two energy modes.

27. A scanning bone densitometer comprising:
   a radiation source collimated to produce a beam of radiation having a divergence of less than ten degrees;
   a patient support supporting a supine patient with the patient's head and feet lying along a longitudinal axis;
   a radiation detector positioned with respect to the radiation source to receive the beam of radiation passing through a patient held by the patient support;
   a scanning assembly moving the radiation source and radiation detector along a series of transverse scan paths substantially perpendicular to the longitudinal axis across the patient to acquire a plurality of scan images having a diverging region of overlap; and
   an electronic computer communicating with the radiation detector and executing a stored program to:
      (i) determine the height of a structure within the diverging region of overlap;
      (ii) adjust the magnification of at least one scanned image based on the determined height of the structure.

28. A scanning bone densitometer comprising:
   a radiation source collimated to produce a diverging beam of radiation;
   a radiation detector positioned with respect to the radiation source to receive radiation passing through a patient;
   a scanning assembly moving the radiation source and electronic detector along a series of scan paths along across the patient to acquire a plurality of scanned images; and
   an electronic computer communicating with the electronic detector and executing a stored program to:
      (i) determine a degree of image alignment for at least a portion of adjacent given scan images with different overlaps of the adjacent scan images;
      (ii) deducing a structure height of structure within the patient based on beam divergence and the overlap providing the best degree of image alignment; and
      (iii) using the structure height to correct for variation in magnification to the structure;
   whereby increased accuracy of the data of the scan images is provided.

29. The scanning bone densitometer of claim 28 wherein the computer uses the correction of magnification of the structure to correct for quantitative measurements of the patient.

30. The scanning bone densitometer of claim 29 wherein the computer uses the correction of magnification of the structure to correct for quantitative bone-related measurements.

31. The scanning densitometer of claim 28 including a patient support table sized and positioned to support the patient in a supine position positioned between the radiation source and radiation detector.

32. The scanning densitometer of claim 28 wherein the radiation source and radiation detector are positioned to provide a space wherein the patient may stand during a scanning of the patient by the scanning assembly.

33. The scanning densitometer of claim 28 wherein the patient support supports a supine patient with the patient's head and feet lying along a longitudinal axis and wherein the scanning assembly moves the radiation source and radiation detector along a series of transverse scan paths substantially perpendicular to the longitudinal axis across the patient to acquire the scan images.

34. The scanning densitometer of claim 28 further wherein the radiation source is collimated to produce a fan beam of radiation and wherein the radiation detector is a linear array of detector elements.

35. The densitometer of claim 34 wherein the linear array of detector elements are CZT detector elements.

36. The densitometer of claim 34 wherein the linear array of detector elements are stacked layers of scintillators having different energy sensitivities each associated with a photodetector.

37. The densitometer of claim 34 wherein the linear array of detector elements are side by side rows of scintillators having different energy sensitivities each associated with a photodetector.

38. The scanning densitometer of claim 28 wherein the radiation source is an x-ray tube having a switched voltage to produce sequentially different x-ray energies.

39. The scanning densitometer of claim 28 wherein the radiation source is poly-energetic radiation beam filtered with a K-edge filter to form two energy modes.

* * * * *